(12) United States Patent  (10) Patent No.: US 7,935,111 B2
 MacDonald  (45) Date of Patent: May 3, 2011

(54) ELECTROSURGERY PENCIL

(75) Inventor: Bruce MacDonald, Kitchener (CA)

(73) Assignee: AMT Electrosurgery Inc. (CA)

( * ) Notice: Subject to any disclaimer, the term of this patent is extended or adjusted under 35 U.S.C. 154(b) by 0 days.

(21) Appl. No.: 11/669,706

(22) Filed: Jan. 31, 2007

(65) Prior Publication Data

US 2007/0198009 A1    Aug. 23, 2007

Related U.S. Application Data

(60) Provisional application No. 60/743,193, filed on Jan. 31, 2006.

(51) Int. Cl.
*A61B 18/14* (2006.01)
(52) U.S. Cl. .................. 606/42; 606/45; 606/49
(58) Field of Classification Search .............. 606/42, 606/45, 49
See application file for complete search history.

(56) References Cited

U.S. PATENT DOCUMENTS

| 5,374,188 | A  | * | 12/1994 | Frank et al. ........................ 433/32 |
| 5,916,231 | A  | * | 6/1999  | Bays ............................... 606/180 |
| 6,293,945 | B1 | * | 9/2001  | Parins et al. ..................... 606/45 |
| 6,298,550 | B1 | * | 10/2001 | Kirwan, Jr. ....................... 606/52 |
| 6,346,078 | B1 | * | 2/2002  | Ellman et al. .................. 600/235 |
| 6,447,510 | B1 | * | 9/2002  | Ellman et al. .................... 606/45 |

FOREIGN PATENT DOCUMENTS

DE         3409061        *  4/1995

* cited by examiner

*Primary Examiner* — Lee S Cohen
(74) *Attorney, Agent, or Firm* — Zeman-Mullen & Ford, LLP

(57) ABSTRACT

An electrosurgery pencil having a bent or angled portion which enables a physician to easily perform surgical procedures without his or her hand obstructing the view of the surgical site.

12 Claims, 3 Drawing Sheets

ELECTROSURGERY PENCIL

CROSS-REFERENCE TO RELATED APPLICATIONS

This application claims the benefit of an earlier filed provisional application having Ser. No. 60/743,193 and filed on Jan. 31, 2006, which is herein incorporated in its entirety.

FIELD OF INVENTION

This invention relates generally to electrosurgery pencils for use in electrosurgery procedures and, more particularly, and electrosurgery pencil having various angles which enables a surgeon to perform surgical procedures without obstructing his or her view of the surgical site while holding the electrosurgery pencil.

BACKGROUND OF THE INVENTION

Many electrosugrey pencils exist in the prior art. However, these prior art electrosurgery pencils have straight shafts and the physician's hand is often in the way while trying to see and cut away tissue from the surgical site. Most times, a physician will need to angle his or her hand to one side while cutting with existing electrosurgery pencils.

Accordingly, there is a need for an electrosurgery pencil that enables a physician to have a better line of sight to the cutting area in surgical procedures where a physician's line of sight is obstructed, without the need to awkwardly position his or her hand to see where and how they are cutting with the electrosurgery pencil.

SUMMARY OF THE INVENTION

This invention is directed to an electrosurgery pencil which enables a physician to easily perform surgical procedures without his or her hand obstructing the view of the surgical site. The electrosurgery pencil includes a handpiece having a first end, a second opposite end, and at least one bent or angled portion of the handpiece located between the first end and the second opposite end, and an electrosurgery electrode coupled to the first end of the handpiece.

In one exemplary embodiment, the bent portion (which is also defined to mean curved portion) or angled portion of the handpiece comprises a bayonet like shape. If the handpiece includes an angled portion, it may include at least two angles greater than ninety degrees, at least two angles equal to ninety degrees, or at least two angles less than ninety degrees.

BRIEF DESCRIPTION OF THE DRAWINGS

The present invention is hereafter described in conjunction with the following drawing figures, wherein like numerals denote like elements, and.

DETAILED DESCRIPTION OF EXEMPLARY EMBODIMENTS

The following description is of exemplary embodiments of the invention only, and is not intended to limit the scope, applicability or configuration of the invention in any way. Rather, the following description is intended to provide a convenient illustration for implementing various embodiments of the invention. As will become apparent, various changes may be made in arrangement of the elements described in these embodiments without departing from the scope of the invention set forth in the appended claims. For example, in the context of the present invention, the apparatus hereof may include only those elements shown in FIGS. 2 and 3 but may also include additional elements as those described with reference to FIG. 6. Likewise, the same is true with the exemplary embodiments shown in FIGS. 4 and 5 in that these exemplary embodiments may also include additional elements as those described with reference to FIG. 6. Furthermore, any of the exemplary embodiments shown and described may include a number of varying configurations, sizes, and circumferences for the handpiece.

Figure 1:
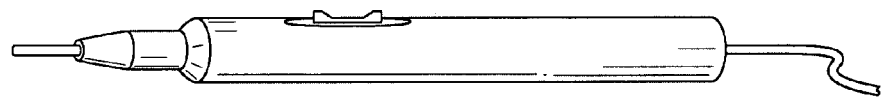
FIG. 1 is a top perspective view of a prior art electrosurgery pencil.

In general, the present invention provides an electrosurgery pencil having one or more bends, curves, or angles, which enables a physician to more easily perform surgical procedures without his or her hand obstructing the view of the surgical site. FIG. 1 shows a prior art electrosurgery pencil having a straight handpiece with first and second ends and an electrosurgery electrode coupled to one of the ends. An exemplary embodiment of the electrosurgery pencil of the present invention is illustrated in FIG. 2.

Figure 2:
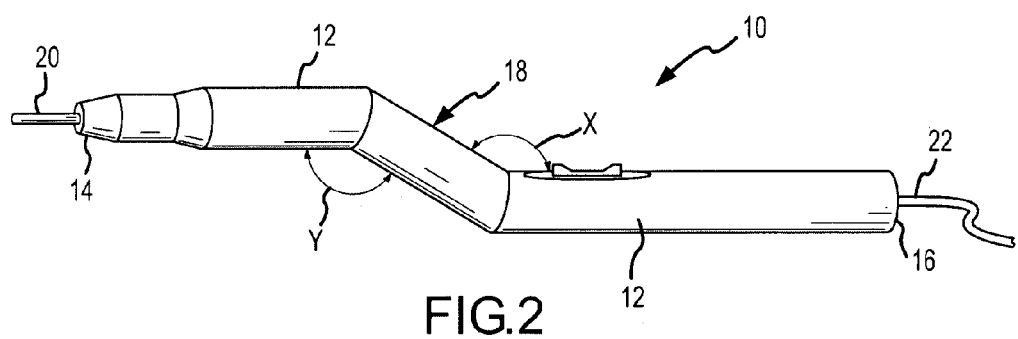
FIG. 2 is a top perspective view of an exemplary electrosurgery pencil according to the present invention.

Electrosurgery pencil 10 shown in FIG. 2 includes a handpiece 12 having a first end 14 and a second end 16 located opposite first end 14, and at least one angled portion 18 of handpiece 12 located between first end 14 and second end 16. Electrosurgery pencil 10 also includes an electrosurgery electrode 20 coupled to the first end 14 of handpiece 12. Handpiece 12 may be comprised of a plastic or any other material that is suitable for its intended use. The interior of handpiece 12 may be the same or similar to any other prior art electrosurgical pencil with the exception of its configuration and shape which follows, and is in direct alignment with, the configuration and shape of the exterior of the handpiece shown in FIGS. 2 and 3.

Handpiece 12 may be of varying lengths but angled portion 18 of handpiece 12 is preferably shorter in length than that portion of handpiece 12 located between angled portion 18 and second end 16 in order to provide more stability and accuracy to the movement of the electrosurgery electrode 20 during electrosurgery. In the exemplary embodiment of electrosurgery pencil 10 shown in FIG. 2, angled portion 18 of handpiece 12 comprises a bayonet like shape having two angles (angle X and angle Y) measuring greater than ninety degrees.

Figure 3:
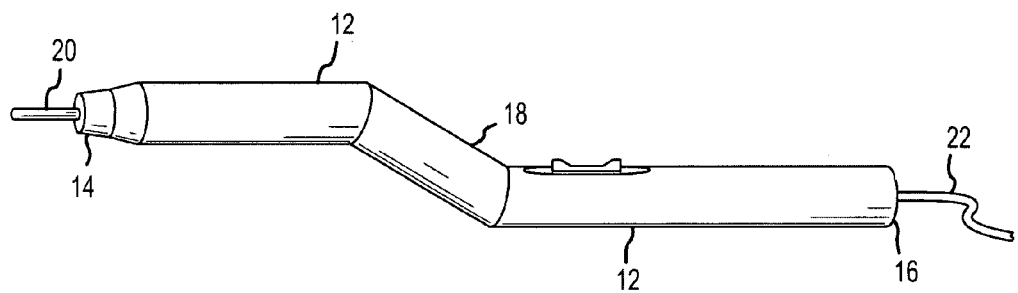
FIG. 3 is a side elevational view of the electrosurgery pencil shown in FIG. 2.

FIG. 3 is a side elevation view of the exemplary electrosurgery pencil 10 illustrated in FIG. 2 showing handpiece 12 having first end 14, second end 16, angled portion 18, and electrosurgery electrode 20 coupled to first end 14 of handpiece 12. Second end 16 of handpiece 12 is coupled to an electrical cord or power cord 22 which is used to provide electricity or power to the electrosurgery pencil 10.

Figure 4:
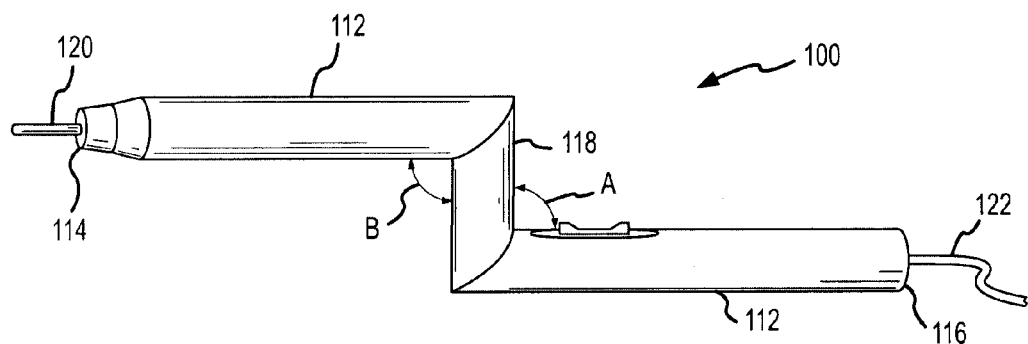
FIG. 4 is a side elevational view of another exemplary embodiment of the electrosurgery pencil of the present invention.
Figure 5:
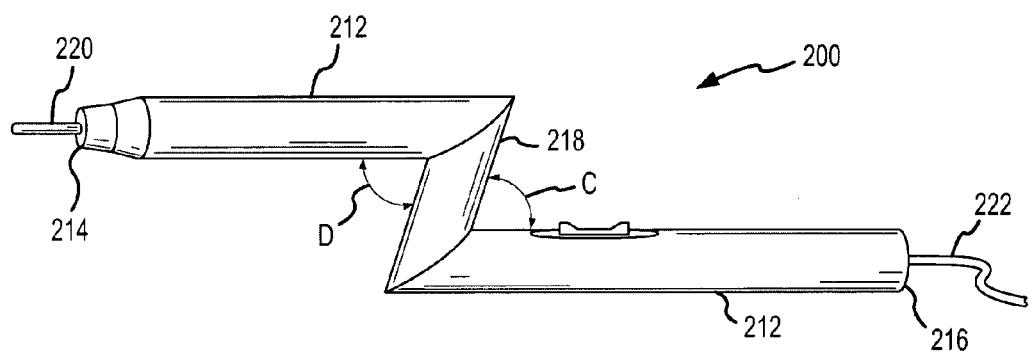
FIG. 5 is a side elevational view of still another exemplary embodiment of the electrosurgery pencil of the present invention.

FIGS. 4 and 5 show additional exemplary embodiments of the electrosurgery pencil of the present invention. Electrosurgery pencil 100 shown in FIG. 4 includes a handpiece 112 having a first end 114 and a second end 116 located opposite first end 114, and at least one angled portion 118 of handpiece 112 located between first end 114 and second end 116. An electrosurgery electrode 120 is coupled to the first end 114 of handpiece 112. Second end 116 of handpiece 112 is coupled to an electrical cord or power cord 122 which is used to provide electricity or power to the electrosurgery pencil 100.

Handpiece 112 may be of varying lengths but angled portion 118 of handpiece 112 is preferably shorter in length than that portion of handpiece 112 located between angled portion 118 and second end 116 in order to provide more stability and accuracy to the movement of electrosurgery electrode 120 during electrosurgery. In the exemplary embodiment of electrosurgery electrode 100 shown in FIG. 4, angled portion 118 of handpiece 112 comprises a step like shape having two right angles (angle A and angle B) measuring ninety degrees.

Electrosurgery pencil 200 shown in FIG. 5 includes a handpiece 212 having a first end 214 and a second end 216 located opposite first end 214, and at least one angled portion 218 of handpiece 212 located between first end 214 and second end 216. Electrosurgery pencil 200 also includes an electrosurgery electrode 220 coupled to the first end 214 of the handpiece 212. Second end 216 of handpiece 212 is coupled to an electrical cord or power cord 222 which is used to provide electricity or power to the electrosurgery pencil 200.

Handpiece 212 may be of varying lengths but angled portion 218 of handpiece 212 is preferably shorter in length than that portion of handpiece 212 located between angled portion 218 and second end 216 in order to provide more stability and accuracy to the movement of electrosurgery electrode 220 during electrosurgery. In the exemplary embodiment of electrosurgery pencil 200 shown in FIG. 5, angled portion 218 of handpiece 212 comprises a sharp bayonet like shape having two angles (angle C and angle D) measuring less than ninety degrees.

Figure 6:
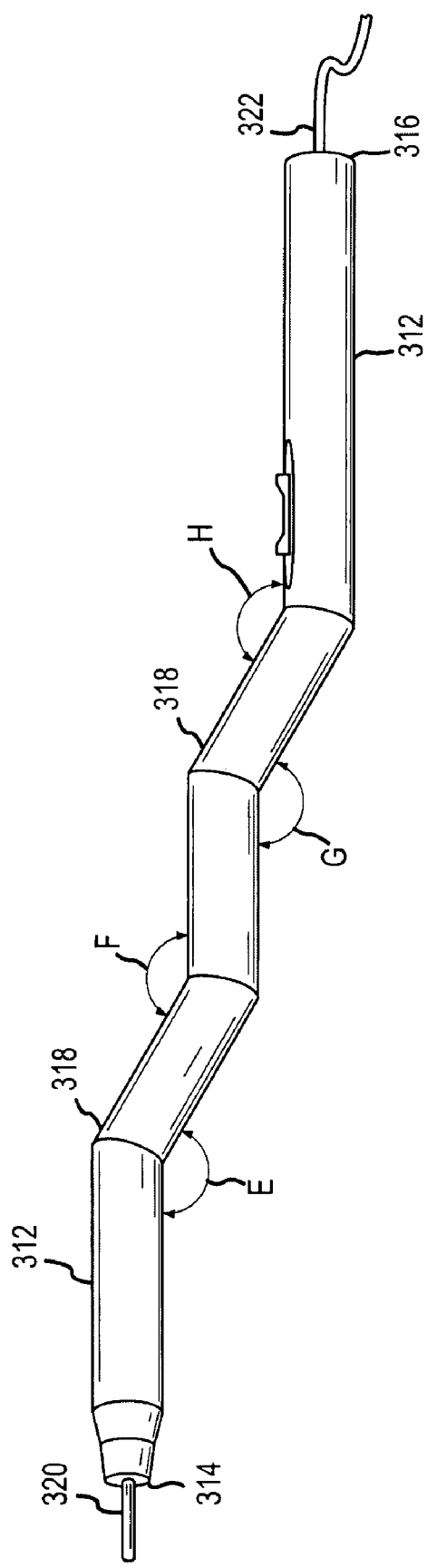
FIG. 6 is a side elevational view of yet another exemplary embodiment of the electrosurgery pencil of the present invention.

FIG. 6 is a side elevational view of yet another exemplary embodiment of the electrosurgery pencil 300 of the present invention. Electrosurgery pencil 300 includes a handpiece 312 having a first end 314 and a second end 316 located opposite first end 314, and two angled portions 318 of handpiece 312 located between first end 314 and second end 316. Electrosurgery pencil 300 also includes an electrosurgery electrode 320 coupled to the first end 314 of the handpiece 312. Second end 316 of handpiece 312 is coupled to an electrical cord or power cord 322 which is used to provide electricity or power to the electrosurgery pencil 300.

Handpiece 312 may be of varying lengths but combined angled portions 318 of handpiece 312 are preferably shorter in length than that portion of handpiece 312 located between angled portions 318 and second end 316 in order to provide more stability and accuracy to the movement of electrosurgery electrode 320 during electrosurgery. In the exemplary embodiment of electrosurgery pencil 300 shown in FIG. 6, angled portions 318 of handpiece 312 comprise a staggered bayonet like shape having four angles (angle E, angle F, angle G and angle H) each measuring greater than ninety degrees.

The electrosurgery pencil of the present invention may be single use or reusable. In addition, activation of the electrosurgery pencil of the present invention may be performed by push button, rocker switch, or foot pedal. The electrosurgery pencil of the present invention may be a monopolar device that is designed to work with a return electrode. It may work with all standard monopolar electrosurgical devices which operate in the frequency range of 330,000 hz to 1,000,000 hz (1 megaherz). The electrosurgery pencil of the present invention is also capable of working with all conventional electrodes.

The foregoing description is of exemplary embodiments of the subject invention. It will be appreciated that the foregoing description is not intended to be limiting; rather, the exemplary embodiments set forth herein merely set forth some exemplary applications of the subject invention. It will be appreciated that various changes, deletions, and additions may be made to the components and steps discussed herein without departing from the scope of the invention as set forth in the appended claims.

The invention claimed is:

1. An electrosurgery pencil comprising:
   a handpiece having a first end, a second end opposite the first end, at least one angled portion located between the first end and the second opposite end, and means for activating the handpiece located between the second opposite end and the at least one angled portion of the handpiece, wherein said handpiece has a uniform diameter throughout the at least one angled portion and said at least one angled portion of the handpiece is positioned above a portion of the handpiece located between the at least one angled portion and the second opposite end of the handpiece; and
   an electrosurgery electrode coupled to the first end of the handpiece.

2. The electrosurgery pencil of claim 1 wherein the second opposite end of the handpiece is coupled to a power cord for providing power to the electrosurgery pencil.

3. The electrosurgery pencil of claim 1 wherein the handpiece comprises a bayonet like shape.

4. The electrosurgery pencil of claim 1 wherein the at least one angled portion of the handpiece comprises two angles greater then 90 degrees.

5. The electrosurgery pencil of claim 1 wherein the at least one angled portion of the handpiece comprises two 90 degree angles.

6. The electrosurgery pencil of claim 1 wherein the at least one angled portion of the handpiece comprises two angles less then 90 degrees.

7. The electrosurgery pencil of claim 1 wherein the handpiece comprises two angled portions located between the first end and the second opposite end of the handpiece.

8. An electrosurgery pencil for use in electrosurgery comprising:
   a handpiece having a first end, a second end opposite the first end, and two angled portions located between the first end and the second opposite end wherein the two angled portions are positioned above a portion of the handpiece located between the two angled portions and the second opposite end of the handpiece; and
   an electrosurgery electrode coupled to the first end of the handpiece.

9. The electrosurgery pencil of claim 8 wherein the handpiece has a uniform diameter throughout the two angled portions of the handpiece.

10. The electrosurgery pencil of claim 9 wherein the two angled portions of the handpiece each comprise two approximate angles greater than 90 degrees.

11. The electrosurgery pencil of claim 9 wherein the two angled portions of the handpiece each comprise two approximate 90 degree angles.

12. The electrosurgery pencil of claim 9 wherein the two angled portions of the handpiece each comprise two approximate angles less than 90 degrees.

* * * * *